US012605213B2

(12) United States Patent
Mino et al.

(10) Patent No.: US 12,605,213 B2
(45) Date of Patent: Apr. 21, 2026

(54) PROCEDURE GUIDANCE FOR SAFETY

(71) Applicant: Olympus Corporation, Tokyo (JP)

(72) Inventors: Hiroyuki Mino, Westborough, MA (US); Hirokazu Horio, Allentown, PA (US); Kazuhiro Gono, Hachioji (JP)

(73) Assignee: Olympus Corporation, Tokyo (JP)

( * ) Notice: Subject to any disclaimer, the term of this patent is extended or adjusted under 35 U.S.C. 154(b) by 196 days.

(21) Appl. No.: 18/047,520

(22) Filed: Oct. 18, 2022

(65) Prior Publication Data

US 2023/0122179 A1 Apr. 20, 2023

Related U.S. Application Data

(60) Provisional application No. 63/263,715, filed on Nov. 8, 2021, provisional application No. 63/262,791, filed on Oct. 20, 2021.

(51) Int. Cl.
*A61B 34/10* (2016.01)
*G16H 10/60* (2018.01)
*G16H 40/20* (2018.01)
*G16H 70/20* (2018.01)

(52) U.S. Cl.
CPC ............. *A61B 34/10* (2016.02); *G16H 10/60* (2018.01); *G16H 40/20* (2018.01); *G16H 70/20* (2018.01); *A61B 2034/104* (2016.02); *A61B 2034/105* (2016.02); *A61B 2034/107* (2016.02)

(58) Field of Classification Search
CPC .............. A61B 34/10; A61B 2034/104; A61B 2034/105; A61B 2034/107; A61B 34/20; A61B 34/25; A61B 90/30; A61B 2034/256; A61B 2090/365; G16H 10/60; G16H 40/20; G16H 70/20; G16H 20/40; G06N 3/044; G06N 3/0464; G06N 3/047; G06N 3/08; G06N 5/01; G06N 20/10
See application file for complete search history.

(56) References Cited

U.S. PATENT DOCUMENTS

2022/0370138 A1* 11/2022 Shelton, IV ........... G16H 40/67

* cited by examiner

*Primary Examiner* — Chinyere Mpamugo
(74) *Attorney, Agent, or Firm* — Schwegman Lundberg & Woessner, P.A.

(57) ABSTRACT

Systems, devices, and methods for providing a computer-assisted endoscopic procedure guidance are disclosed. A procedure planning system can generate an endoscope navigation plan for a patient scheduled for an endoscopic procedure performed by an operating physician. The system comprises a processor that can access an endoscopic procedure database, identify therefrom physicians substantially matching the experience level of the operating physician, and retrieve reference procedure data of the past procedures performed by the matching physicians. The reference procedure data can be further selected from past procedures performed on patients with similar medical information to the scheduled patient. The processor can generate an endoscope navigation plan for the scheduled patient using reference procedure data. The endoscope navigation plan can be displayed along with the live endoscopic image to guide the operating physician in performing the procedure.

20 Claims, 9 Drawing Sheets

301
306
322
322
312
307
308
324
309

PROCEDURE GUIDANCE FOR SAFETY

CROSS REFERENCE TO RELATED APPLICATIONS

This application is related to commonly assigned U.S. Provisional Patent Application Ser. No. 63/263,715, entitled "PROCEDURE GUIDANCE FOR SAFETY", filed on Nov. 8, 2021, U.S. Provisional Patent Application Ser. No. 63/262,791, entitled "PROCEDURE GUIDANCE FOR SAFETY", filed on Oct. 20, 2021, which are incorporated by reference in their entirety.

FIELD OF THE DISCLOSURE

The present document relates generally to endoscopic systems, and more particularly to computer-assisted endoscopic procedure guidance based on past procedure data and information about physician experience.

BACKGROUND

Endoscopes have been used in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices or biological matter collection devices for sampling or treating an anatomical region, and providing suction passageways for collecting fluids (e.g., saline or other preparations), among other procedures. Examples of such anatomical region can include gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

In endoscopy, the distal portion of the endoscope can be configured for supporting and orienting a therapeutic device, such as with the use of an elevator. In some systems, two endoscopes can work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path.

Peroral cholangioscopy is a technique that permits direct endoscopic visualization, diagnosis, and treatment of various disorders of patient biliary and pancreatic ductal system using miniature endoscopes and catheters inserted through the accessory port of a duodenoscope. Peroral cholangioscopy can be performed by using a dedicated cholangioscope that is advanced through the accessory channel of a duodenoscope, as used in Endoscopic Retrograde Cholangio-Pancreatography (ERCP) procedures. ERCP is a technique that combines the use of endoscopy and fluoroscopy to diagnose and treat certain problems of the biliary or pancreatic ductal systems, including the liver, gallbladder, bile ducts, pancreas, or pancreatic duct. In ERCP, an cholangioscope (also referred to as an auxiliary scope, or a "daughter" scope) can be attached to and advanced through a working channel of a duodenoscope (also referred to as a main scope, or a "mother" scope). Typically, two separate endoscopists operate each of the "mother-daughter" scopes. Although biliary cannulation can be achieved directly with the tip of the cholangioscope, most endoscopists prefer cannulation over a guidewire. A tissue retrieval device can be inserted through the cholangioscope to retrieve biological matter (e.g., gallstones, bill duct stones, cancerous tissue) or to manage stricture or blockage in bile duct.

Peroral cholangioscopy can also be performed by inserting a small-diameter dedicated endoscope directly into the bile duct, such as in a Direct Per-Oral Cholangioscopy (DPOC) procedure. In DPOC, a slim endoscope (cholangioscope) can be inserted into patient mouth, pass through the upper GI tract, and enter into the common bile duct for visualization, diagnosis, and treatment of disorders of the biliary and pancreatic ductal systems.

Physician experience and dexterity plays a significant role in determining a success rate and patient outcome in endoscopic procedures like ERCP and DPOC. A computer-assisted endoscopic procedure guidance can be especially helpful for inexperienced physicians.

SUMMARY

The present disclosure recognizes several technological problems to be solved with endoscopes, such as duodenoscopes used for diagnostics and retrieval of sample biological matter. One of such problems is increased difficulty in navigating endoscopes, and instruments inserted therein, to locations in anatomical regions deep within a patient. For example, in ERCP procedures, as the duodenoscope, the cholangioscope, and the tissue retrieval device become progressively smaller due to being inserted sequentially in progressively smaller lumens, it has become more difficult to maneuver and navigate the endoscope through the patient anatomy, maintain endoscope stabilization, and maintain correct cannulation position in a narrow space (e.g., the bile duct). It can also be difficult to maintain an appropriate cannulation angle due to limited degree of freedom in scope elevator. Cannulation and endoscope navigation require advanced surgical skills and manual dexterity, which can be particularly challenging for less-experienced operating physicians (e.g., surgeons or endoscopists).

Another challenge in endoscopy is a high degree of variability of patient anatomy, especially patients with surgically altered or otherwise difficult anatomy. For example, in ERCP procedures, some patients may have altered anatomy to a portion of the GI tract or the pancreaticobiliary system (e.g., the ampulla). In some patients, stricture ahead of pancreas can compress the stomach and part of duodenum, making it difficult to navigate the duodenoscope in a limited lumen of the compressed duodenum and to navigate the cholangioscope to reach the duodenal papilla, the point where the dilated junction of the pancreatic duct and the bile duct (ampulla of Vater) enter the duodenum. In another example, some patients have alternated papilla anatomy. With the duodenoscope designed to be stable in the duodenum, it can be more difficult to reach the duodenal papilla in surgically altered anatomy. Endoscopic systems generally lack the capability of providing cannulation and endoscope navigation guidance based on patient's unique anatomy.

In ERCP, anatomical structure, position, and shape of the duodenal papilla, or location of blood vessels therein, may vary across patients. A cannulation and navigation strategy suited for one patient may not be optimal for another. In addition to such inter-patient variations, endoscopy surgeons generally have different experiences, skills, or preferences in performing ERCP or DPOC procedures. For example, what is deemed an "easy" cannulation and navigation strategy for an experienced physician may not be as easily performed and ultimately adopted by another physician with less experience in the field. Such inter-physician variations in their experience, dexterity, or preferences can play an important role affecting the procedure outcome especially in patients with difficult or surgically altered anatomies.

The present disclosure can help solve these and other problems by providing systems, devices, and methods for determining an endoscope navigation plan suited for a patient scheduled for an endoscopic procedure performed by an operating physician (e.g., a surgeon or endoscopist). The endoscope navigation plan can be determined based on past procedures done by the same or similar physicians and/or in the same patients or different patients having similar anatomical structures. According to one embodiment disclosed herein, a procedure planning system can comprise a processor that can access an endoscopic procedure database, identify therefrom one or more physicians substantially matching the experience level of the operating physician, and retrieve procedure data of the past procedures (e.g., a reference endoscopic image or navigation parameters) performed by the matching physicians. In some examples, the reference procedure data can be further identified as those acquired from past procedures performed on patients whose medical information (e.g., anatomical structure) substantially matches the medical information of the scheduled patient. Based on the reference procedure data, the processor can generate an endoscope navigation plan for the scheduled patient. Real-time procedure data (e.g., endoscopic image or navigation parameters) from a live procedure on the scheduled patient can be displayed along with the reference procedure data. The operating physician can adjust cannulation or navigation in accordance with the reference procedure data. In response to the real-time navigation parameter significantly deviating from the reference navigation parameter value, the system can generate an alert to the physician, or automatically adjust the real-time navigation parameter.

The computer-assisted endoscopic procedure guidance based on the information about the operating physician's specialty and experience level and optionally medical information of the scheduled patient, as described in various embodiments in this disclosure, can help provide a more effective endoscope navigation plan suited for each individual patient and also suited for the physician performing the procedure. The computer-assisted endoscopic navigation planning can improve the treatment quality, patient safety, and overall success rate of endoscopic procedures. The computer-assisted endoscopic navigation plans can be used by physicians of different experience levels, and help reduce the burden for manual surgical planning, and improve the prognostic predictability of the endoscopic procedures.

Example 1 is a system for planning an endoscopic procedure of a type to be performed on a scheduled patient by an operating physician. The system comprises a processor configured to: determine an experience level of the operating physician; access an endoscopic procedure database to retrieve therefrom reference procedure data associated with one or more matching physicians having respective experience levels substantially matching the experience level of the operating physician, the endoscopic procedure database comprising procedure data of past endoscopic procedures of the type performed by a plurality of physicians on a plurality of patients; and generate an endoscope navigation plan for the scheduled patient using the reference procedure data so as to improve at least one of a treatment quality, patient safety, or a success rate of the endoscopic procedure.

In Example 2, the subject matter of Example 1 optionally includes a sensing apparatus configured to acquire procedure data during the endoscopic procedure performed on the scheduled patient; and an output unit configured to generate a navigation feedback using the acquired procedure data and the endoscope navigation plan.

In Example 3, the subject matter of any one or more of Examples 1-2 optionally includes the processor that can be further configured to: access the endoscopic procedure database to retrieve therefrom procedure data associated with procedures performed on one or more matching patients having medical information substantially matching medical information of the scheduled patient; and retrieve the reference procedure data corresponding to at least one endoscopic procedure performed on at least one of the matching patients by at least one of the matching physicians.

In Example 4, the subject matter of Example 3 optionally includes the medical information of the scheduled patient that can include demographics and health condition, and the procedure data stored in the endoscopic procedure database include demographics and health condition of the plurality of patients, and the processor that can be configured to identify the one or more matching patients having respective demographics and health condition substantially similar to the demographics and health condition of the scheduled patient.

In Example 5, the subject matter of any one or more of Examples 3-4 optionally includes the medical information of the scheduled patient that can include anatomy information, and the procedure data stored in the endoscopic procedure database include anatomy information of the plurality of patients, and the processor that can be configured to identify the one or more matching patients having respective anatomy information substantially similar to the patient anatomy of the scheduled patient.

In Example 6, the subject matter of Example 5 optionally includes the medical information of the scheduled patient that can include an image or image features of an anatomical target, the procedure data stored in the endoscopic procedure database include respective images or image features of the anatomical target obtained from the plurality of patients, and the processor that can be configured to identify the one or more matching patients having respective images or image features substantially similar to the images or image features of the scheduled patient.

In Example 7, the subject matter of any one or more of Examples 1-6 optionally includes, wherein to generate the endoscope navigation plan includes to estimate, from the reference procedure data, one or more reference endoscope navigation parameters including: a distance of an endoscope distal portion relative to an anatomical target; a heading direction of the endoscope distal portion relative to the anatomical target; an angle of cannula or a surgical element; a protrusion amount of a cannula or a surgical element; a speed or force applied to the endoscope distal portion or to a surgical element; a rotational direction or a cutting area of a surgical element; or a projected navigation path toward the anatomical target.

In Example 8, the subject matter of Example 7 optionally includes the reference procedure data that can include at least one reference endoscopic image taken during an endoscopic procedure performed by one of the matching physicians, and wherein the processor is configured to determine the one or more endoscope navigation parameters using the at least one reference endoscopic image.

In Example 9, the subject matter of any one or more of Examples 3-8 optionally includes the reference procedure data that can include at least one reference endoscopic image acquired during an endoscopic procedure performed on one of the matching patients by one of the matching physicians. The system further comprises a sensing apparatus configured to acquire procedure data including an endoscopic image acquired from the scheduled patient during the endoscopic procedure, and an output unit configured to display the endoscopic image of the scheduled patient and the reference endoscopic image.

In Example 10, the subject matter of Example 9 optionally includes the output unit that can be further configured to display one or more visual indications overlaid upon the endoscopic image of the scheduled patient, the one or more visual indications including: an anatomical target; a reference navigation path toward the anatomical target; or a progress of the endoscope toward the anatomical target along the reference navigation path.

In Example 11, the subject matter of any one or more of Examples 9-10 optionally includes the output unit that can be configured to display the endoscopic image of the scheduled patient transparently or semi-transparently superimposed over the reference endoscopic image.

In Example 12, the subject matter of any one or more of Examples 9-11 optionally includes the processor that can be configured to generate the endoscope navigation plan including one or more reference endoscope navigation parameters by applying the endoscopic image of the scheduled patient to a trained machine-learning (ML) model, the trained ML model being trained to establish a relationship between endoscopic images and one or more endoscope navigation parameters.

In Example 13, the subject matter of Example 12 optionally includes the processor that can be configured to train the ML model using a training dataset comprising reference procedure data stored in the endoscopic procedure database, the reference procedure data including (i) stored reference endoscopic images of the matching patients acquired during respective endoscopic procedures performed by the matching physicians, and (ii) stored endoscope navigation parameters for the respective endoscopic procedures.

In Example 14, the subject matter of any one or more of Examples 9-13 optionally includes the processor that can be configured to: generate the endoscope navigation plan including determining one or more reference endoscope navigation parameters using the reference procedure data; and measure one or more real-time navigation parameters from the procedure data acquired from the scheduled patient; and the output unit is configured to generate a navigation feedback based on a comparison between the one or more real-time navigation parameters and the one or more reference endoscope navigation parameters.

In Example 15, the subject matter of Example 14 optionally includes the navigation feedback that can include an alert to the operating physician in response to the one or more real-time navigation parameters deviates from the one or more reference endoscope navigation parameters by a specific margin.

In Example 16, the subject matter of any one or more of Examples 14-15 optionally includes a navigation controller configured to automatically adjust the one or more real-time navigation parameters based on the comparison between the one or more real-time navigation parameters and the one or more reference endoscope navigation parameters.

Example 17 is a method of planning an endoscopic procedure using an image-guided endoscopic system. The method comprises steps of: receiving information about an experience level of an operating physician performing an endoscopic procedure on a scheduled patient; accessing an endoscopic procedure database to retrieve therefrom reference procedure data associated with one or more matching physicians having respective experience levels substantially matching the experience level of the operating physician, the endoscopic procedure database comprising procedure data of past endoscopic procedures performed by a plurality of physicians on a plurality of patients; and generating an endoscope navigation plan for the scheduled patient using the reference procedure data so as to improve at least one of a treatment quality, patient safety, or a success rate of the endoscopic procedure.

In Example 18, the subject matter of Example 17 optionally includes acquiring procedure data during the endoscopic procedure performed on the scheduled patient; and generating a navigation feedback based on the acquired procedure data and the endoscope navigation plan.

In Example 19, the subject matter of any one or more of Examples 17-18 optionally includes accessing the endoscopic procedure database to retrieve therefrom procedure data associated with procedures performed on one or more matching patients having medical information substantially matching medical information of the scheduled patient, wherein retrieving the reference procedure data includes retrieving procedure data corresponding to at least one endoscopic procedure performed on at least one of the matching patients by at least one of the matching physicians.

In Example 20, the subject matter of Example 19 optionally includes the medical information of the scheduled patient that can include one or more of: demographics and health condition; anatomy information; or an image or image features of an anatomical target.

In Example 21, the subject matter of any one or more of Examples 17-20 optionally includes generating the endoscope navigation plan by estimating, from the reference procedure data, one or more reference endoscope navigation parameters.

In Example 22, the subject matter of Example 21 optionally includes the reference procedure data that can include at least one reference endoscopic image taken during an endoscopic procedure performed by one of the matching physicians, and wherein estimating the one or more endoscope navigation parameters is by using the at least one reference endoscopic image.

In Example 23, the subject matter of any one or more of Examples 19-22 optionally includes the procedure data of the scheduled patient that can include an endoscopic image acquired during the endoscopic procedure, and the reference procedure data include at least one reference endoscopic image acquired during an endoscopic procedure performed on one of the matching patients by one of the matching physicians, the method further comprising displaying the endoscopic image of the scheduled patient and the reference endoscopic image.

In Example 24, the subject matter of Example 23 optionally includes displaying one or more visual indications overlaid upon the endoscopic image of the scheduled patient, the one or more visual indications including: an anatomical target; a reference navigation path toward the anatomical target; or a progress of the endoscope toward the anatomical target along the reference navigation path.

In Example 25, the subject matter of any one or more of Examples 23-24 optionally includes displaying the endoscopic image of the scheduled patient transparently or semi-transparently superimposed over the reference endoscopic image.

In Example 26, the subject matter of any one or more of Examples 23-25 optionally includes: measuring one or more real-time navigation parameters from the procedure data acquired from the scheduled patient; estimating one or more reference endoscope navigation parameters using the reference procedure data; and generating a navigation feedback based on a comparison between the one or more real-time navigation parameters and the one or more reference endoscope navigation parameters.

In Example 27, the subject matter of Example 26 optionally includes estimating one or more reference endoscope navigation parameters by applying the endoscopic image of the scheduled patient to a trained machine-learning (ML) model, the trained ML model being trained to establish a relationship between endoscopic images and one or more endoscope navigation parameters.

In Example 28, the subject matter of any one or more of Examples 26-27 optionally includes automatically adjusting the one or more real-time navigation parameters based on the comparison between the one or more real-time navigation parameters and the one or more reference endoscope navigation parameters.

The presented techniques are described in terms of health-related procedures, but are not so limited. This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

DETAILED DESCRIPTION

Figure 1:
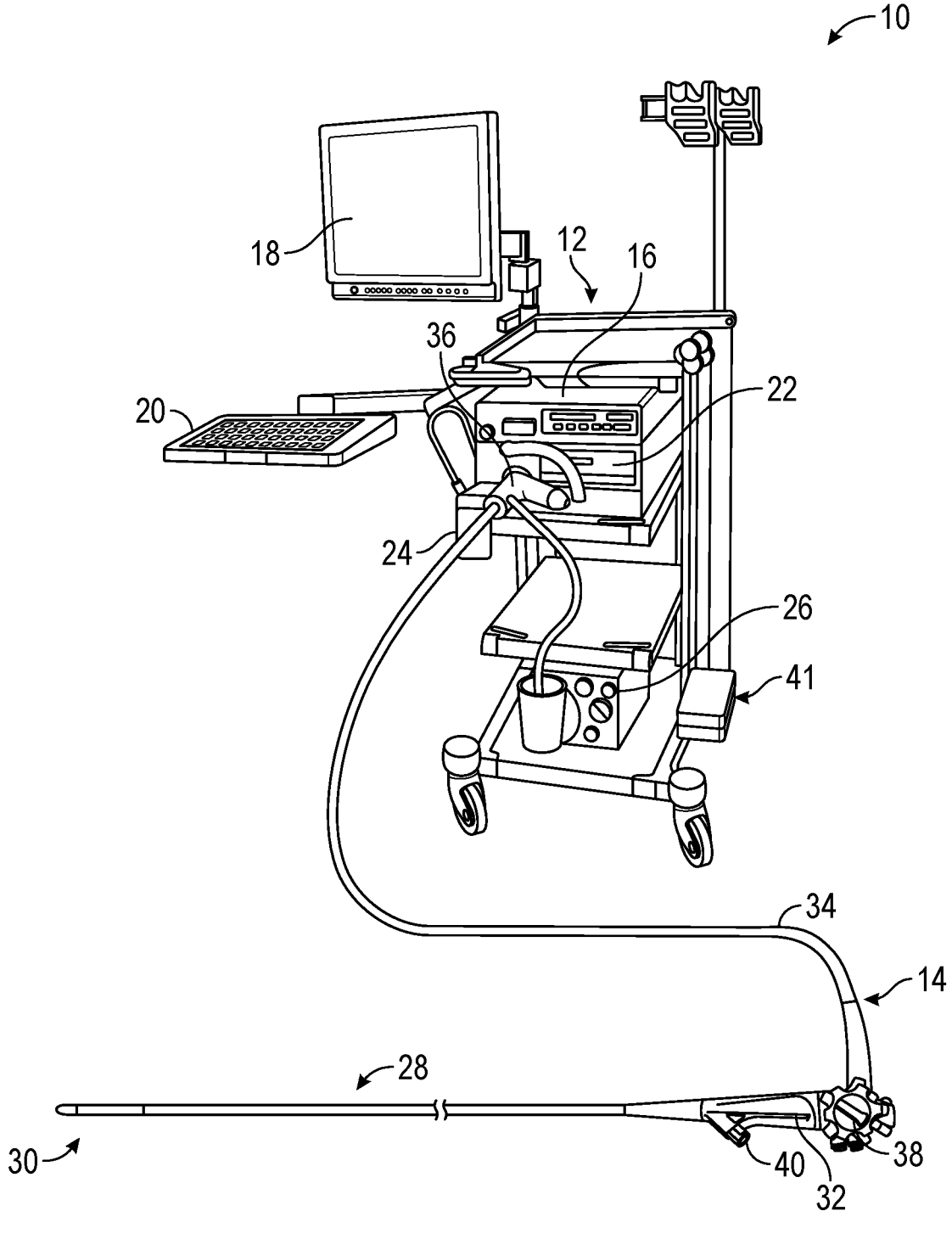
FIGS. 1-2 are schematic diagrams illustrating an example of an endoscopy system for use in endoscopic procedures such as an ERCP procedure.

This document describes systems, devices, and methods for computer-assisted endoscopic procedure guidance based on past procedure data and information about physician specialty and experience level, and optionally patient medical information. According to one embodiment, a procedure planning system can generate an endoscope navigation plan for a patient scheduled for an endoscopic procedure performed by an operating physician. The system comprises a processor that can identify, from an endoscopic procedure database, physicians substantially matching the experience level of the operating physician, and retrieve from the database reference procedure data of the past procedures performed by the matching physicians. The reference procedure data can be further selected from past procedures performed on patients with similar medical information to the scheduled patient. The processor can generate an endoscope navigation plan for the scheduled patient using reference procedure data. The endoscope navigation plan can be displayed along with the live endoscopic image to guide the operating physician in performing the procedure FIG. 1 is a schematic diagram illustrating an example of an endoscopy system 10 for use in endoscopic procedures, such as an ERCP procedure. The system 10 comprises an imaging and control system 12 and an endoscope 14. The endoscopy system 10 is an illustrative example of an endoscopy system suitable for patient diagnosis and/or treatment using the systems, devices and methods described herein, such as tethered and optically enhanced biological matter and tissue collection, retrieval and storage devices and biopsy instruments that can be used for obtaining samples of tissue or other biological matter to be removed from a patient for analysis or treatment of the patient. According to some examples, the endoscope 14 can be insertable into an anatomical region for imaging and/or to provide passage of or attachment to (e.g., via tethering) one or more sampling devices for biopsies, or one or more therapeutic devices for treatment of a disease state associated with the anatomical region.

The imaging and control system 12 can comprise a control unit 16, an output unit 18, an input unit 20, a light source 22, a fluid source 24, and a suction pump 26. The imaging and control system 12 can include various ports for coupling with endoscopy system 10. For example, the control unit 16 can include a data input/output port for receiving data from and communicating data to the endoscope 14. The light source 22 can include an output port for transmitting light to the endoscope 14, such as via a fiber optic link. The fluid source 24 can comprise one or more sources of air, saline or other fluids, as well as associated fluid pathways (e.g., air channels, irrigation channels, suction channels) and connectors (barb fittings, fluid seals, valves and the like). The fluid source 24 can be in communication with the control unit 16, and can transmit one or more sources of air or fluids to the endoscope 14 via a port. The fluid source 24 can comprise a pump and a tank of fluid or can be connected to an external tank, vessel or storage unit. The suction pump 26 can comprise a port used to draw a vacuum from the endoscope 14 to generate suction, such as for withdrawing fluid from the anatomical region into which the endoscope 14 is inserted.

The output unit 18 and the input unit 20 can be used by an operator of endoscopy system 10 to control functions of endoscopy system 10 and view output of endoscope 14. In some examples, the control unit 16 can additionally be used to generate signals or other outputs for treating the anatomical region into which the endoscope 14 is inserted. Examples of such signals or outputs can include electrical output, acoustic output, a radio-frequency energy output, a fluid output and the like for treating the anatomical region with, for example, cauterizing, cutting, freezing and the like.

The endoscope 14 can interface with and connect to the imaging and control system 12 via a coupler section 36. In the illustrated example, the endoscope 14 comprises a duodenoscope that may be use in a ERCP procedure, though other types of endoscopes can be used with the features and teachings of the present disclosure. The endoscope 14 can comprise an insertion section 28, a functional section 30, and a handle section 32, which can be coupled to a cable section 34 and the coupler section 36.

Figure 4:
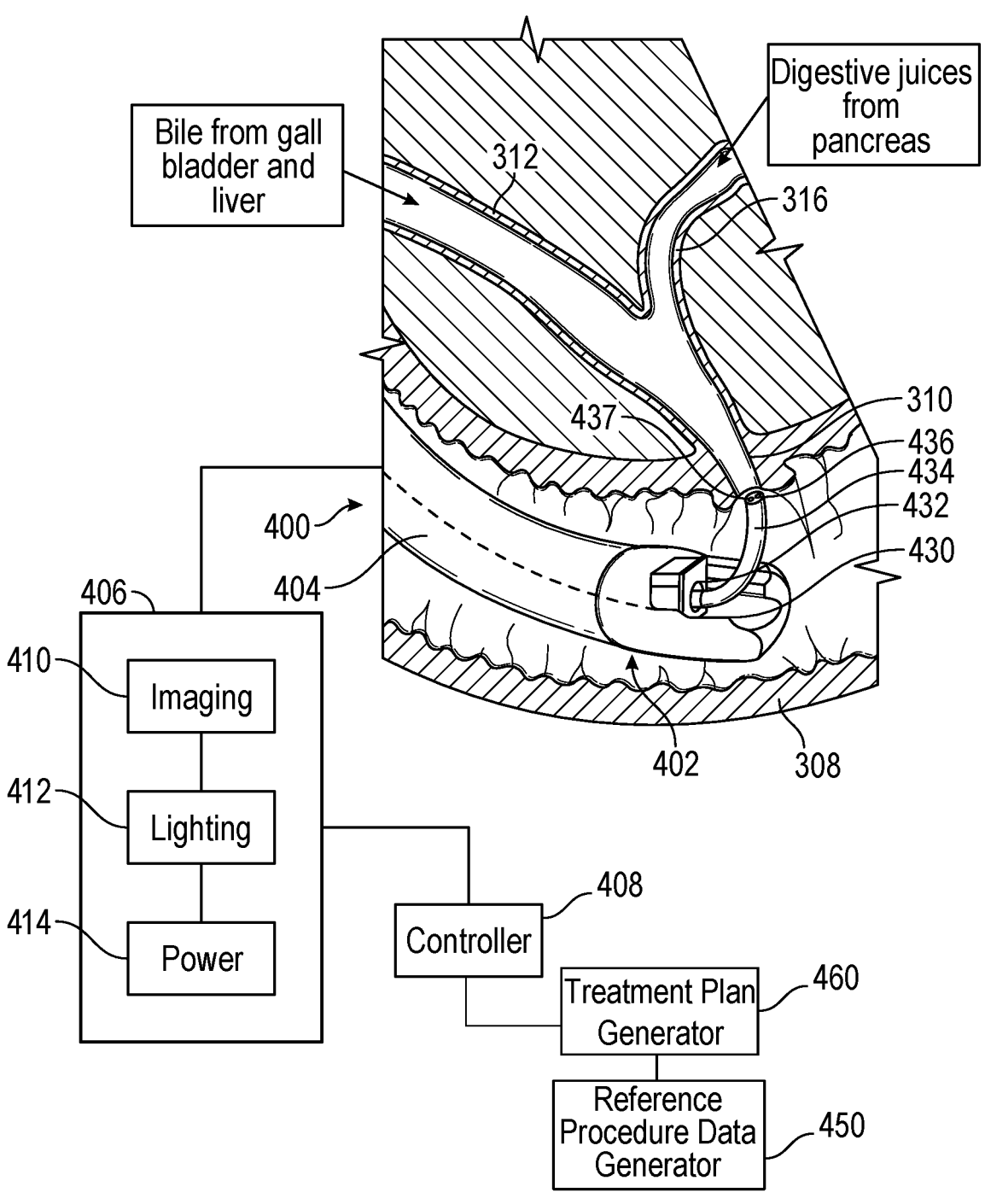
FIG. 4 is a diagram illustrating an example of mother-daughter endoscopes used in an ERCP procedure, and a portion of patient anatomy where the procedure is performed.

The insertion section 28 can extend distally from the handle section 32, and the cable section 34 can extend proximally from the handle section 32. The insertion section 28 can be elongate and include a bending section, and a distal end to which functional section 30 can be attached. The bending section can be controllable (e.g., by control knob 38 on the handle section 32) to maneuver the distal end through tortuous anatomical passageways (e.g., stomach, duodenum, kidney, ureter, etc.). Insertion section 28 can also include one or more working channels (e.g., an internal lumen) that can be elongate and support insertion of one or more therapeutic tools of functional section 30, such as a cholangioscope as shown in FIG. 4. The working channel can extend between handle section 32 and functional section 30. Additional functionalities, such as fluid passages, guide wires, and pull wires can also be provided by insertion section 28 (e.g., via suction or irrigation passageways, and the like).

The handle section 32 can comprise a control knob 38 and ports 40. The ports 40 can be configured to couple various electrical cables, guide wires, auxiliary scopes, tissue collection devices of the present disclosure, fluid tubes and the like to handle section 32 for coupling with insertion section 28. The control knob 38 can be coupled to a pull wire, or other actuation mechanisms, extending through insertion section 28. The control knob 38 can be used by a user to manually advance or retreat the insertion section 28 of the endoscope 14, and to adjust bending of a bending section at the distal end of the insertion section 28. In some examples, an optional drive unit 46 (FIG. 2) can be used to provide motorized drive for advancing a distal section of endoscope 14 under the control of the control unit 16.

The imaging and control system 12, according to examples, can be provided on a mobile platform (e.g., cart 41) with shelves for housing light source 22, suction pump 26, image processing unit 42 (FIG. 2), etc. Alternatively, several components of the imaging and control system 12 shown in FIGS. 1 and 2 can be provided directly on the endoscope 14 such that the endoscope is "self-contained."

The functional section 30 can comprise components for treating and diagnosing anatomy of a patient. The functional section 30 can comprise an imaging device, an illumination device, and an elevator. The functional section 30 can further comprise optically enhanced biological matter and tissue collection and retrieval devices. For example, the functional section 30 can comprise one or more electrodes conductively connected to handle section 32 and functionally connected to the imaging and control system 12 to analyze biological matter in contact with the electrodes based on comparative biological data stored in the imaging and control system 12. In other examples, the functional section 30 can directly incorporate tissue collectors.

Figure 2:
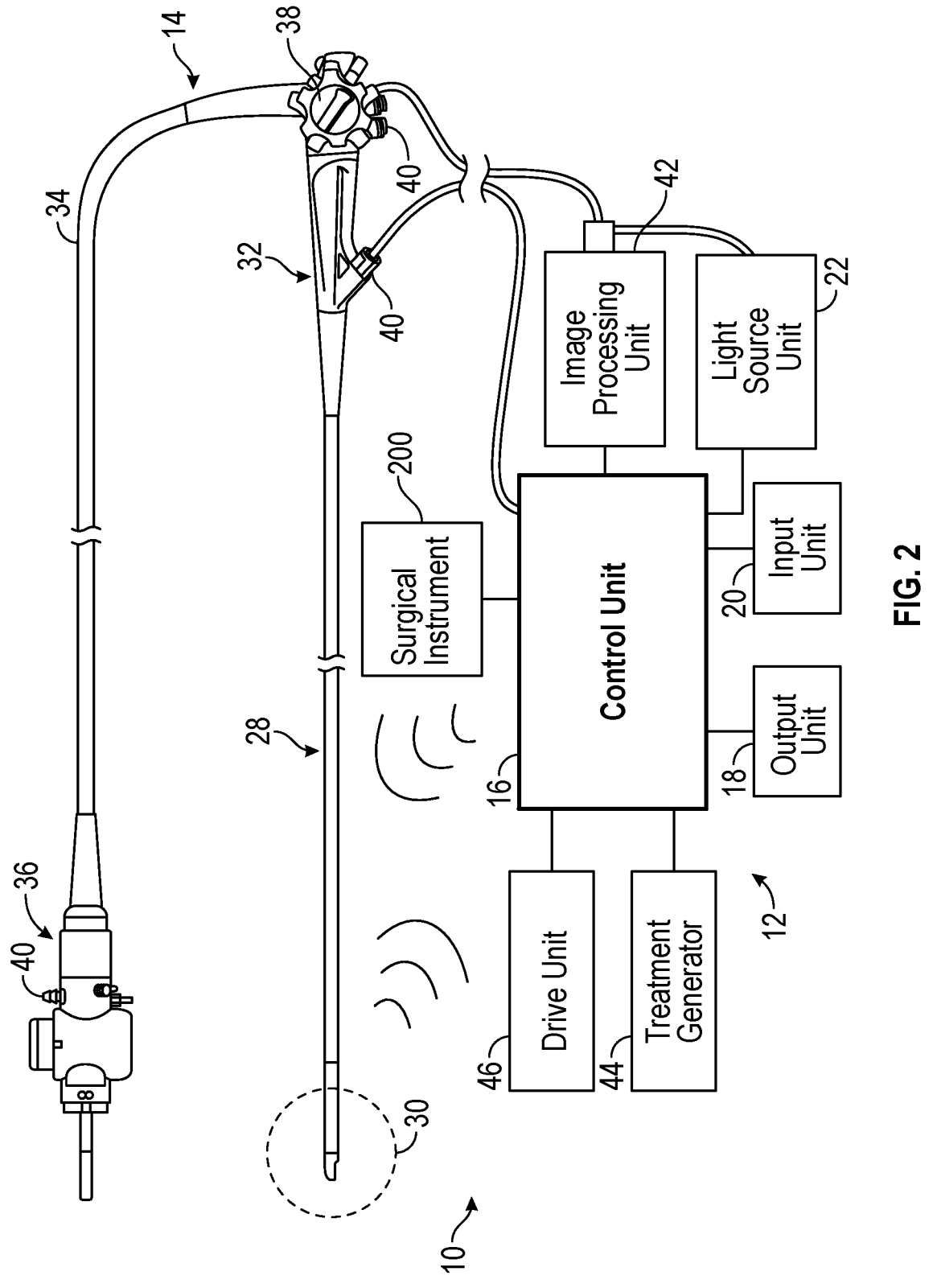

FIG. 2 is a schematic diagram of the endoscopy system 10 shown in FIG. 1, which comprises the imaging and control system 12 and the endoscope 14. FIG. 2 schematically illustrates components of the imaging and control system 12 coupled to the endoscope 14, which in the illustrated example comprises a duodenoscope. The imaging and control system 12 can comprise a control unit 16, which can include or be coupled to an image processing unit 42, a treatment generator 44, and a drive unit 46, as well as the light source 22, the input unit 20, and the output unit 18 as discussed above with reference to FIG. 1. The control unit 16 can comprise, or can be in communication with, a surgical instrument 200 comprising a device configured to engage tissue and collect and store a portion of that tissue and through which an imaging device (e.g., a camera) can view target tissue via inclusion of optically enhanced materials and components. The control unit 16 can be configured to activate an imaging device (e.g., a camera) at the functional section of the endoscope 14 to view target tissue distal of surgical instrument 200 and endoscopy system 10, which can be fabricated of a translucent material to minimize the impacts of the camera being obstructed or partially obstructed by the tissue retrieval device. Likewise, the control unit 16 can be configured to activate the light source 22 to shine light on the surgical instrument 200, which can include select components that are configured to reflect light in a particular manner, such as tissue cutters being enhanced with reflective particles.

The image processing unit 42 and the light source 22 can each interface with the endoscope 14 (e.g., at the functional section 30) by wired or wireless electrical connections. The imaging and control system 12 can accordingly illuminate an anatomical region using the light source 22, collect signals representing the anatomical region, process signals representing the anatomical region using the image processing unit 42, and display images representing the anatomical region on the output unit 18. The imaging and control system 12 can include the light source 22 to illuminate the anatomical region using light of desired spectrum (e.g., broadband white light, narrow-band imaging using preferred electromagnetic wavelengths, and the like). The imaging and control system 12 can connect (e.g., via an endoscope connector) to the endoscope 14 for signal transmission (e.g., light output from light source, video signals from the imaging device such as positioned at the distal portion of the endoscope 14, diagnostic and sensor signals from a diagnostic device, and the like).

The treatment generator 44 can generate a treatment plan, which can be used by the control unit 16 to control the operation of the endoscope 14, or to provide with the operating physician a guidance for maneuvering the endoscope 14, during an endoscopic procedure on the scheduled patient. In an example, the treatment generator 44 can generate an endoscope navigation plan using reference procedure data (e.g., endoscopic images or navigation parameters) of past procedures performed by physicians substantially matching the expertise and experience level of the operating physician. In some examples, the reference procedure data can be further identified as those acquired from past procedures performed on patients whose medical information (e.g., anatomical structure) substantially matches the medical information of the scheduled patient. The reference procedure data may be retrieved from an endoscopic procedure database. The endoscope navigation plan include suggested parameter values that can help guide the operating physician to cannulate and navigate the endoscope in the patient anatomy. Examples of generating an endoscope navigation plan using reference procedure data retrieved from a procedure database and using the endoscope navigation plan to guide endoscopic procedure are discussed below with reference to FIGS. 4-5.

Figure 3A:
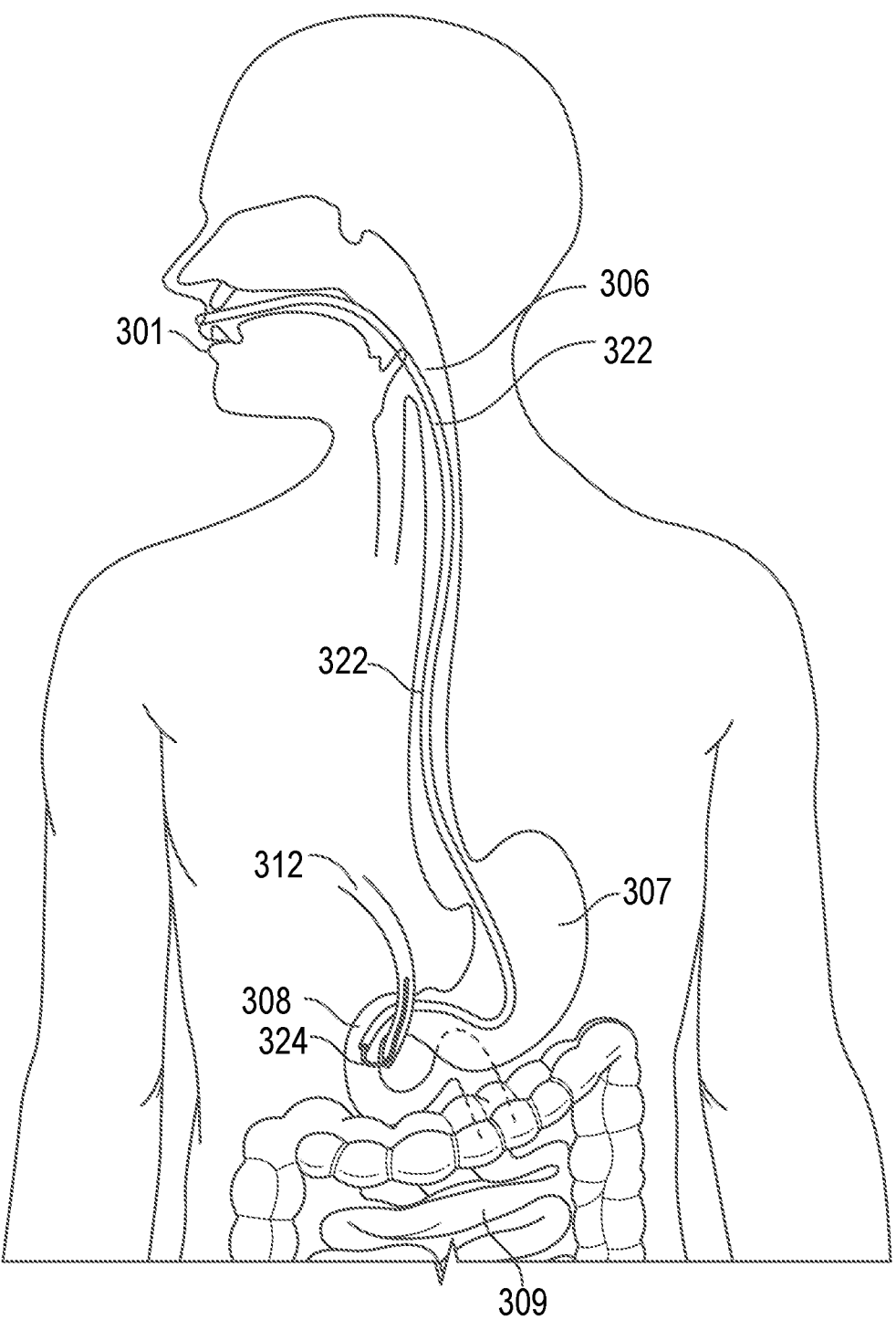
FIGS. 3A-3B are diagrams illustrating an example of peroral cholangioscopy involving direct insertion of a cholangioscope into patient bile duct as in a DPOC procedure, and a portion of patient anatomy where the procedure is performed.
Figure 3B:
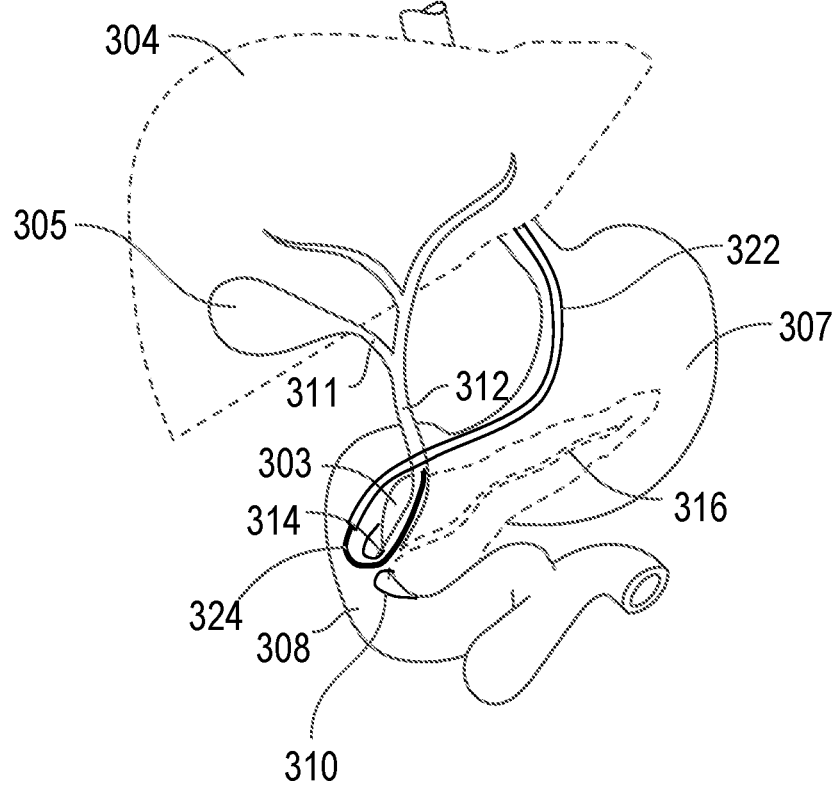

FIGS. 3A-3B are diagrams illustrating an example of peroral cholangioscopy performed via direct insertion of a cholangioscope 324 into the bile duct, as in a DPOC procedure, and a portion of patient anatomy where the procedure is performed. The cholangioscope 324 is nested inside of a guide sheath 322, and inserted perorally into a patient to reach duodenum 308. Duodenum 308 comprises an upper part of the small intestine. The guide sheath 322 can extend into mouth 301, through esophagus 306, through stomach 307 to reach the duodenum 308. Before reaching intestines 309, the guide sheath 322 can position the cholangioscope 324 proximate common bile duct 312. The common bile duct 312 carries bile from the gallbladder 305 and liver 304, and empties the bile into the duodenum 308 through sphincter of Oddi 310 (FIG. 3B). The cholangioscope 324 can extend from guide sheath 322 to extend into common bile duct 312. In some examples, steering features of guide sheath 322 (e.g., pull wire) can be used to facilitate navigating and bending of cholangioscope 324 through stomach 307, in addition to direct steering of cholangioscope 324 via the pull wires. For example, navigation of the Pyloric canal and Pyloric sphincter can be difficult to navigate using only an endoscope. Thus, the guide sheath 322 can be used to turn or bend elongate body of cholangioscope 324, or reduce the amount of steering or bending of the elongate body of the cholangioscope 324 required by pull wires, to facilitate traversing the Pyloric sphincter.

FIG. 3B is a schematic view of duodenum 308 connected to common bile duct 312 via duodenal papilla 314. Common bile duct 312 can branch off into pancreatic duct 316 and gallbladder duct 311. Duodenal papilla 314 can include sphincter of Oddi 310 that controls flow of bile and pancreatic juice into the intestine (duodenum). Pancreatic duct 316 can lead to pancreas 303. Pancreatic duct 316 carries pancreatic juice from pancreas 303 to the common bile duct 312. Gallbladder duct 311 can lead to gallbladder 305. In some patients, it can be difficult to navigate surgical instruments to duodenal papilla 314. It can also be difficult to navigate a surgical instrument into common bile duct 312 via insertion through duodenal papilla 314. Therefore, it is common during medical procedures to cut sphincter of Oddi 310 to enlarge duodenal papilla 314 to allow for easier access of instrument into common bile duct 312.

FIG. 4 is a diagram illustrating an example of mother-daughter endoscopes used in an ERCP procedure, and a portion of patient anatomy where the procedure is performed. The mother-daughter endoscopes comprise an auxiliary scope 434 (cholangioscope) attached to and advanced through a lumen 432 of a main scope 400 (duodenoscope). The auxiliary scope 434 can comprise a lumen 436. The distal portion of the main scope 400 positioned in duodenum 308 comprises a functional module 402, an insertion section module 404, and a control module 406. The control module 406 can include, or be coupled to, a controller 408. Similar to the discussion above with respect to FIG. 1, the control module 406 can include other components, such as those described with reference to endoscopy system 10 (FIG. 1) and control unit 16 (FIG. 2). Additionally, the control module 406 can comprise components for controlling an imaging device (e.g., a camera) and a light source connected to the auxiliary scope 434, such as an imaging unit 410, a lighting unit 412 and a power unit 414. The main scope 400 can be configured similarly as endoscope 14 of FIGS. 1 and 2.

The functional module 402 of the main scope 400 can comprise an elevator portion 430. The auxiliary scope 434 can itself include functional components, such as camera lens 437 and a light lens (not illustrated) coupled to control module 406, to facilitate navigation of the auxiliary scope 434 from the main scope 400 through the anatomy and to facilitate viewing of components extending from lumen 432.

In ERCP, the auxiliary scope 434 can be guided into the sphincter of Oddi 310. Therefrom, a surgeon operating the auxiliary scope 434 can navigate the auxiliary scope 434 through the lumen 432 of the main scope toward the gallbladder 305, liver 304, or other locations in the gastrointestinal system to perform various procedures. In some examples, the auxiliary scope 434 can be used to guide an additional device to the anatomy to obtain biological matter (e.g., tissue), such as by passage through or attachment to lumen 436.

The biological sample matter can be removed from the patient, typically by removal of the additional device from the auxiliary device, so that the removed biological matter can be analyzed to diagnose one or more conditions of the patient. According to several examples, the mother-daughter endoscope assembly (including the main scope 400 and the auxiliary scope 434) can include additional device features, such as forceps or an auger, for gathering and removing cancerous or pre-cancerous matter (e.g., carcinoma, sarcoma, myeloma, leukemia, lymphoma and the like), or performing endometriosis evaluation, biliary ductal biopsies, and the like.

The controller 408 can include, or be coupled to, a reference procedure data generator 450 and a treatment plan generator 460. The treatment plan generator 460, which is an example of the treatment generator 44 as illustrated in FIG. 2, can automatically generate a treatment plan for an operating physician that may be used in an endoscopic procedure (e.g., ERCP) on a scheduled patient. The reference procedure data generator 450 can produce reference procedure data from past procedures of the same type as the procedure to be performed on the scheduled patient. The past procedures can be selected as those performed by the same or similar physicians (the "matching physicians") matching the information of the operating physician, such as the experience level for performing said type of endoscopic procedures. In some examples, the past procedures selected for generating the reference data can be those performed on patients (the "matching patients") substantially matching the medical information (e.g., anatomical structure) of the scheduled patient, and performed by the matching physicians. The reference procedure data can include one or more reference endoscopic images or navigation parameters.

The treatment plan generator 460 can generate a treatment plan, such as an endoscope navigation plan, based at least on the reference procedure data. The endoscope navigation plan can include one or more reference endoscope navigation parameters with respective values. Examples of the navigation parameters can include: a position of the endoscope distal portion (e.g., the functional section 30 of the endoscope 14 as shown in FIG. 1) relative to an anatomical target of interest, such as a distance from the endoscope distal portion to duodenal papilla, a heading direction of the endoscope distal portion relative to the anatomical target, an angle of a cannula or a surgical element used in cannulation, a protrusion amount of a cannula or a surgical element, a speed or force applied to the endoscope distal portion or a surgical element, a rotational direction or a cutting area of a surgical element, or a projected navigation path toward the anatomical target, among others. According to various examples as described in this disclosure, the endoscope navigation plan (e.g., one or more navigation parameters) can be generated or updated using a trained machine-learning (ML) model. The endoscope navigation plan, including the reference endoscopic images and parameters, may be provided to the operating physician as a procedure guide during cannulation and navigation. The computer-assisted physician-specific and/or patient-specific endo- scope navigation plan based on information of matching-physicians and optionally further based on matching-patients can be suited for the operating physician and also suited for each individual patient, ease the procedure planning burden particularly for inexperience physicians, and improve the treatment quality, patient safety, and overall procedure success rate.

Figure 5:
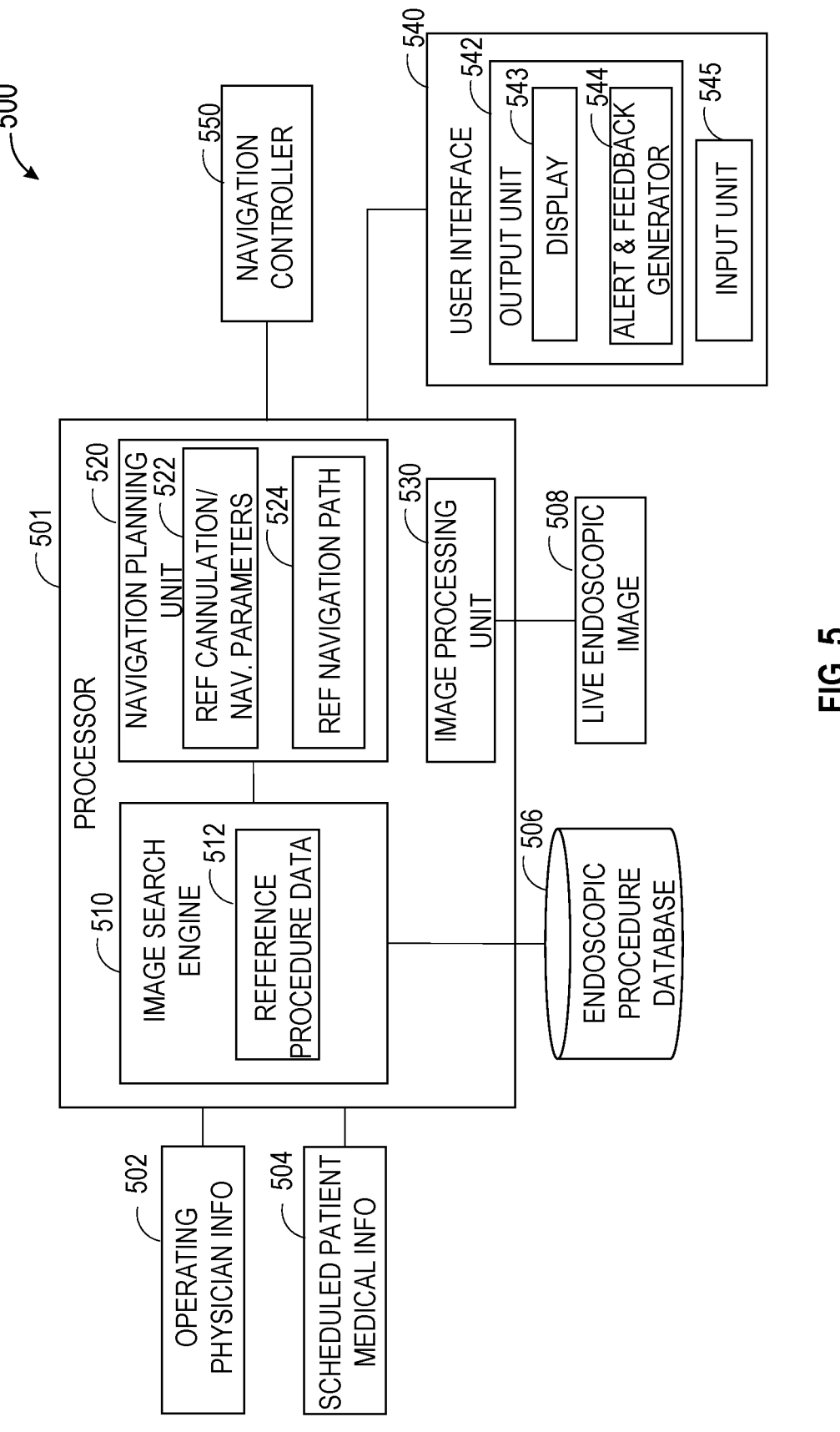
FIG. 5 is a diagram illustrating an example of an image-guided navigation system.

FIG. 5 is a diagram illustrating an example of an image-guided navigation system 500, which can be a part of the control unit 16 in FIG. 1, or the controller 408 along with other associated devices or functional units such as the reference procedure data generator 450 and a treatment plan generator 460 as illustrated in FIG. 4.

The image-guided navigation system 500 can include a processor 501, a user interface device 540, and a navigation controller 550. The processor 501 may include circuit sets comprising one or more other circuits or sub-circuits, including a search engine 510, a navigation planning unit 520, and an image processing unit 530. These circuits may, alone or in combination, perform the functions, methods, or techniques described herein. In an example, the processor 501 and the circuits sets therein may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The search engine 510 can receive operating physician information 502 and optionally medical information 504 of the patient scheduled for an endoscopic procedure of a particular type, such as ERCP, performed by the operating physician. The operating physician information 502 and medical information 504 of the scheduled patient can be provided by a system user prior to the scheduled endoscopic procedure, such as via an input unit 545 on the user interface device 540. Alternatively, such information may be retrieved automatically from an electronic medical record system.

The operating physician information 502 can include the operating physician's experience level for performing endoscopic procedures of the same type as the endoscope procedure to be performed on the scheduled patient. The experience level can be represented by, for example, years in practice, number of procedures of the same type performed in the past (as the endoscope procedure to be performed on the scheduled patient, such as ERCP), and success rate, among others. The scheduled patient medical information 504 can include, for example, patient demographics, health condition and medical history, pre-existing disease, symptoms, location of lesion, among other information. In an example, the scheduled patient medical information 504 can include patient anatomy information, such as images (or video frames) obtained from imaging studies (e.g., X-ray, CT scans, MRI scans, ultrasound, nuclear medicine scans) prior to the scheduled endoscopic procedures. The images can represent anatomy of interest (e.g., duodenal papilla for cannulation into the bile duct), surgically altered anatomy along the cannulation or navigation route, and surrounding anatomical structures. In an example, the images can include patient endoscopic images of the anatomy of interest and endoscopic findings from previous endoscopic procedures. Peri-procedural, live endoscopic images 508 of the patient anatomy of interest can be provided to the search engine 510.

The search engine 510 can query an endoscopic procedure database 506 that stores procedure data of past endoscopic procedures performed by a plurality of physicians on a plurality of patients. The endoscopic procedures can be those of the same type as the endoscopic procedure to be performed on the scheduled patient. The stored procedure data can include, for each procedure, endoscopic images or videos showing patient anatomy, cannulation and endoscope navigation routes, progress of cannulation and navigation, or cannulation or navigation parameters obtained during the procedure or by offline analysis the endoscopic images or videos. Examples of the cannulation or navigation parameters can include: a position of the endoscope distal portion (e.g., the functional section 30 of the endoscope 14 as shown in FIG. 1) relative to an anatomical target of interest, such as a distance from the endoscope distal portion to duodenal papilla, a heading direction of the endoscope distal portion relative to the anatomical target, an angle of a cannula or a surgical element used in cannulation, a protrusion amount of a cannula or a surgical element, a speed or force applied to the endoscope distal portion or a surgical element, a rotational direction or a cutting area of a surgical element, or a projected navigation path toward the anatomical target, among others.

In various examples, the procedure data stored in the endoscopic procedure database 506 may also include physician information and optionally patient medical information for each of the stored past endoscopic procedures. Similar to the operating physician information 502 and the scheduled patient medical information 504 discussed above, the stored physician information can include the corresponding physician's experience level for performing endoscopic procedures of the same type, and the stored patient medical information can include, for example, patient demographics, health conditions information and medical history, patient anatomy, image or image features, etc. In an example, the endoscopic procedure database 506 can organize the procedure data using a lookup table, an association map, or other data structures such that the endoscopic images/videos and cannulation or navigation parameters are indexed by patient information and patient medical information to facilitate searching and procedure data retrieval, as discussed below.

The search engine 510 can search the endoscopic procedure database 506 to identify one or more physicians substantially matching the operating physician information 502 (the "matching physicians"). In an example, the matching physicians are identified as those having substantially similar experience levels to the operating physician for performing the type of endoscopic procedure. The experience level of a physician can have a categorical value (e.g., "high", "medium", or "low") or a numerical value (e.g., 1-5 where a larger number represents a higher level of experience). Alternatively, the experience level can be represented by years of experience of number of procedures of the same or similar type that have been performed and an overall success rate. To search for a matching physician, a matching score can be computed based on the similarity in the experience level (e.g., years of experience, procedures performed thus far, overall success rate) between the operating physician and each of one or more physicians in the endoscopic procedure database 506. A physician is deemed a "matching physician" if the associated matching score satisfies a condition, such as exceeding a threshold. The search engine 510 can retrieve, from the endoscopic procedure database 506, procedure data, hereinafter referred to as reference procedure data 512, that correspond to at least one endoscopic procedure performed by one of the matching physicians.

In some examples, the search engine 510 can further search the endoscopic procedure database 506 to identify one or more patients substantially matching the scheduled patient medical information 504 (the "matching patients"). The matching patients can be identified as those having substantially similar one or more of demographics, health condition, pre-existing illness, medical history, symptoms, patient anatomy, or image or image features to the scheduled patient. To search for a matching patient, a matching score can be computed based on the similarity in medical conditions, demographic information, among other patient information as stated above, between the scheduled patient and each of one or more patients in the endoscopic procedure database 506. A patient is deemed a "matching patient" if the associated matching score satisfies a condition, such as exceeding a threshold. The search engine 510 can further select, from the selected procedures performed by the matching physicians, a subset of endoscopic procedures performed on the matching patients. The search engine 510 can then retrieve the preference procedure data 512 corresponding to at least one endoscopic procedure performed on one of the matching patients by one of the matching physicians.

The navigation planning unit 520, which is an example of the treatment plan generator 460, may generate an endoscope navigation plan with respect to an anatomical target of interest (e.g., duodenal papilla) using the reference procedure data 512. In an example, the reference procedure data 512 include reference endoscopic images/videos, and the navigation planning unit 520 can apply an image processing algorithm (e.g., edge detection) to recognize and localize the target anatomy from the reference image. Alternatively, the anatomical target of interest may be identified manually by the user from the reference image displayed on a user interface.

In an example, the reference procedure data 512 may include reference cannulation or navigation parameters, which are stored in the endoscopic procedure database 506. Alternatively, the navigation planning unit 520 can deter-mine, from the reference image or video, the reference cannulation or navigation parameters 522 and a reference navigation path 524 toward the anatomical target of interest. Examples of the cannulation or navigation parameters can include a position of the endoscope distal portion (e.g., the functional section 30 of the endoscope 14 as shown in FIG. 1) relative to an anatomical target of interest, such as a distance from the endoscope distal portion to duodenal papilla, a heading direction of the endoscope distal portion relative to the anatomical target, an angle of a cannula or a surgical element used in cannulation, a protrusion amount of a cannula or a surgical element, a speed or force applied to the endoscope distal portion or a surgical element, a rotational direction or a cutting area of a surgical element, among others.

In some examples, the navigation planning unit 520 can use artificial intelligence (AI) technology to generate an endoscope navigation plan, including the reference cannulation or navigation parameters 522 and a reference navigation path 524. A machine-learning (ML) model may be trained using procedure data stored in the endoscopic procedure database 506, including procedure data and information about the matching physicians and/or the matching patients as described above. Commonly assigned U.S. Provisional Patent Application Ser. No. 63/263,711, entitled "IMAGE GUIDANCE DURING CANNULATION", filed on Nov. 8, 2021, discusses ML models and using the same to generate a treatment plan, the disclosure of which is hereby incorporated by reference in its entirety. The trained ML model establishes a relationship between images or image features representing variants of the patient anatomy, and endoscope navigation plans (e.g., cannulation or navigation parameters and navigation path) for the variants of the patient anatomy.

The ML model may be trained using supervised learning, unsupervised learning, or reinforcement leaning. Examples of ML model architectures and algorithms may include, for example, decision trees, neural networks, support vector machines, or a deep-learning networks, etc. Examples of deep-learning networks include a convolutional neural network (CNN), a recurrent neural network (RNN) a deep belief network (DBN), or a hybrid neural network comprising two or more neural network models of different types or different model configurations. In an example, the training of a ML model may include constructing a training dataset using selected procedure data of endoscopic procedures performed on a plurality of patients. In an example, the training data can be screened such that only data of procedures performed by the matching physicians, or further the data of procedures performed on matching patients, are included in the training dataset. In an example, the training data can be screened based on a success rate of the procedure, including times of attempts before a successful cannulation or navigation, such that only data of procedures with a desirable success rate achieved within a specified number of attempts are included in the training dataset. In another example, the training data can be screened based on complication associated with the patients. In some examples, particularly in case of a small training dataset (such as due to data screening), the ML model can be trained to generate a treatment plan by extrapolating, interpolating, or bootstrapping the training data, thereby creating a treatment plan specifically tailored to the specific patient and physician. The training of the ML model may be performed continuously or periodically, or in near real time as additional procedure data are made available. The training involves algorithmically adjusting one or more ML model parameters, until the ML model being trained satisfies a specified training convergence criterion.

The trained ML model can be validated, and implemented in an AI-based navigation planning platform. The navigation planning unit 520 may apply the reference images or videos of the patient anatomy to the trained ML model to generate the reference cannulation or navigation parameters 522 and the reference navigation path 524.

The image processing unit 530 can process the live endoscopic images 508 acquired during an endoscopic procedure (e.g., DPOC or ERCP procedure as described above in reference to FIGS. 3A-3B and FIG. 4, respectively), and estimate one or more real-time cannulation or navigation parameters. Examples of the cannulation and navigation parameters can include those mentioned above with respect to the reference cannulation or navigation parameters 522. The processor 501 may compare the real-time navigation parameters with the reference endoscope navigation parameters. As to be discussed further below, the comparison may be presented to the operating physician, who may manually adjust the cannulation or navigation based on said comparison. Additionally or alternatively, a navigation controller 550 may automatically adjust the one or more real-time navigation parameters based on the comparison. For example, if a real-time navigation parameter substantially deviates from the reference navigation parameter value (e.g., beyond a specific margin), then the navigation controller 550 can automatically adjust the real-time navigation parameter until it is within the specific margin of the reference navigation parameter value.

The user interface device 540 can include an output unit 542 and an input unit 545, which are examples of the output unit 18 and the input unit 20 respectively as shown in FIG. 2. The output unit 542 can include a display 543 that can display the reference procedure data 512, such as a reference image. In some examples, the display 543 can display the reference image along with the live endoscopic image 508 of the scheduled patient concurrently. For example, the reference image and the endoscopic image 508 can be displayed side by side. Alternatively, the live endoscopic image 508 can be transparently or semi-transparently superimposed over the reference image. The live endoscopic image 508 may be registered to the reference image with respect to respective landmarks, such that the reference image and the live endoscopic image 508 can be properly aligned.

In some examples, the output unit 542 may display a visual indication of one or more of an anatomical target, a reference navigation direction or path toward the anatomical target, or a progress of the endoscope toward the anatomical target along the reference navigation path. Such visual indication may be displayed overlaid upon the live image, the reference image, or the superimposed image. The visual indication may take the format of include markers, annotations (icons, texts, or graphs), highlights, or animation, among other visual indicators. For example, markers of different shapes, colors, forms, or sizes can be display on the image to distinguish different tissue, anatomical regions, their accessibility or criticality. In some examples, display settings can be adjusted by the user via the input unit 545. An example of image-guided cannulation is discussed below with reference to FIG. 6

The output unit 542 can include an alert and feedback generator 544 that can generate an alert, a notification, or other formats of human-perceptible feedback to the operating physician on the status or progress of the cannulation or navigation in reference to the navigation plan. For example, an alert can be generated to indicate a risk of tissue damage associated with improper cannulation. The feedback can be in one or more forms of audio feedback, visual feedback, or haptic feedback. For example, a proximity sensor on the endoscope can measure a distance to a critical anatomical target. When the endoscope tip enters or comes closer to a "critical zone" as indicated by the measured distance being shorter than a threshold, the critical zone can be displayed in different colors to represent the proximity of the endoscope tip to the anatomical target, such as a green zone, a yellow zone, and a red zone as the endoscope gets closer and closer to the anatomical target. Additionally or alternatively, human-perceptible haptic feedback such as touch or vibration may be generated and provided to the operating physician. The alert and feedback generator 544 can automatically adjust the vibration strength according to the distance to the critical zone. For example, a low vibration can be generated when the endoscope tip is in a green zone. If the system predicts, based on present advancing speed and direction of the endoscope, that the endoscope tip will reach the critical zone in a time less than a predetermined threshold, then the alert and feedback generator 544 can apply moderate vibration when the endoscope tip reaches the yellow zone, and apply high vibration when the endoscope tip reaches the red zone to indicate a heightened risk of tissue damage.

In an example, the route of an endoscope (or other steerable elongate instrument such as a guidewire) can be displayed in one color and overlaid upon the pre-operative images. Once insertion of the endoscope starts, the actual, live navigation path can be displayed in a different color over the planned navigation route. In case of distraction, an alert may be generated to notify the physician such effect. Cannulation or navigation parameters, such as distance to duodenal papilla, can be displayed in real-time on the display 543 to indicate the progress of the procedure. In some examples, the output unit 542 may provide real-time recommendations for adjusting the cannulation or navigation. Once the cannulation is completed successfully, an audio, visual, or haptic confirmation can be generated and provided to the physician. The image-guided endoscopic procedure and real-time alert and feedback as described in this disclosure can improve cannulation and endoscope navigation accuracy and efficiency and procedure success rate, especially for inexperienced physicians.

Figure 6:
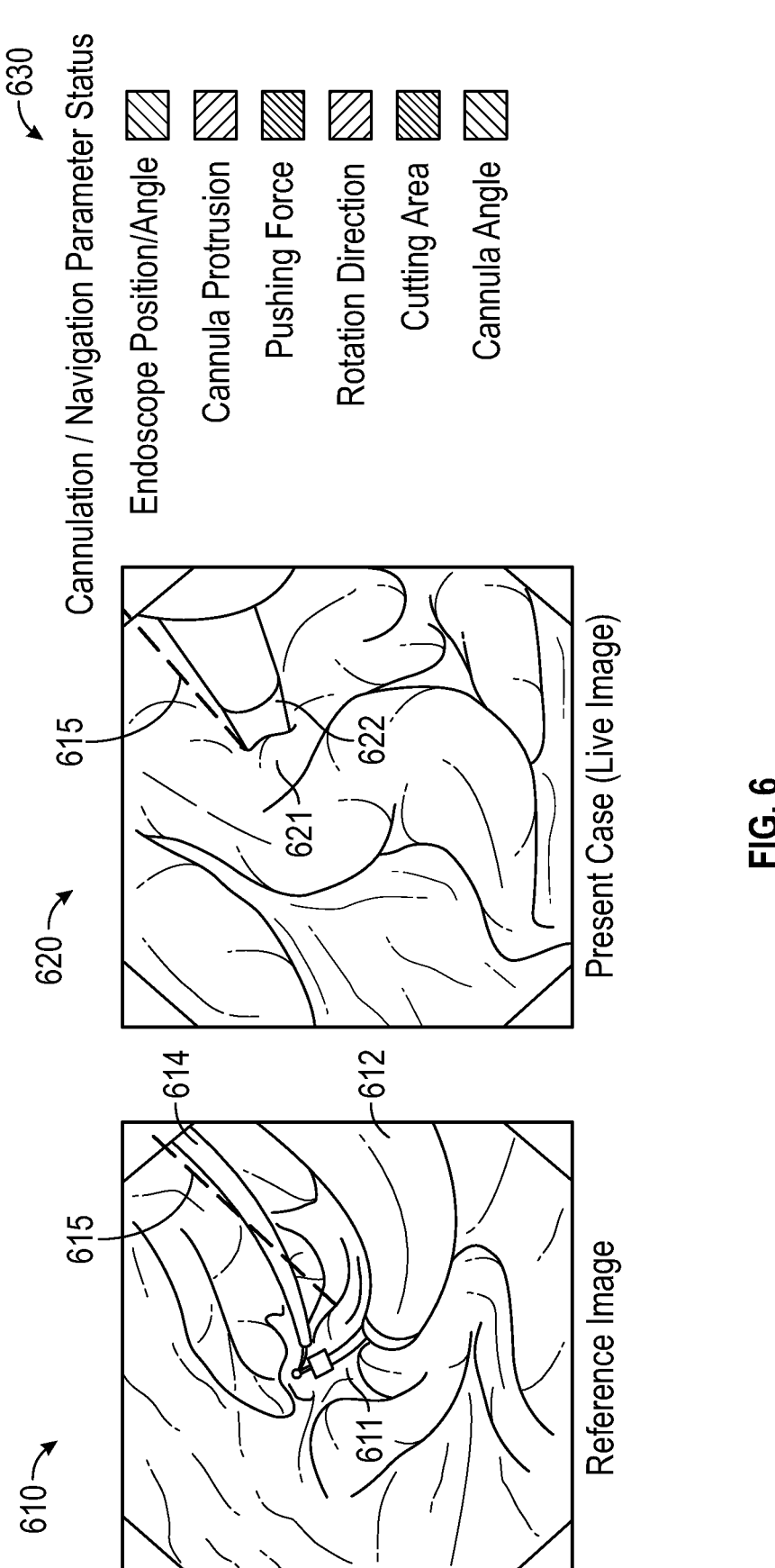
FIG. 6 is a diagram illustrating an example of an image-guided cannulation to access patient pancreaticobiliary system via duodenal papilla.

FIG. 6 illustrates an example of an image-guided cannulation to access patient pancreaticobiliary system via duodenal papilla. A reference endoscopic image 610 is displayed side by side with a live endoscopic image 620, such as on the display 543. The live endoscopic image 620 is taken during a procedure performed on the scheduled patient by an operating physician. The reference endoscopic image 610 is retrieved from the endoscopic procedure database 506, and represents a past endoscopic procedure of the same type that is performed on a matching patient having similar medical information to the scheduled patient and by a matching physician having a similar experience level to the operating physician, as described above with reference to FIG. 5. The reference endoscopic image 610 and the live image 620 can be calibrated and aligned, as discussed above.

The reference endoscopic image 610 and the live image 620 show respectively the anatomical structure of interest, including a duodenal papilla 611 in the reference procedure and a duodenal papilla 621 in the live procedure in this example. The reference image 610 also shows a papillotomy knife 612 and a cannula 614. Reference cannulation or navigation parameters, such as positions and directions of the papillotomy knife 612 and the cannula 614 with respect to the duodenal papilla 611, can also be displayed on the image. By way of example, a reference cannula angle 615 is shown. The live image 620 shows a papillotomy knife 622. To determine a proper cannulation strategy (e.g., a cannula angle) at the duodenal papilla 621 in the live procedure, the reference cannula angle 615 can be superimposed over the live image 620. The operating physician may use the reference cannula angle 615 as a visual guide to cannulate the duodenal papilla 621.

In addition or alternative to the reference cannula angle 615, one or more other reference cannulation or navigation parameters may be displayed and superimposed over the live image 620. For example, a reference navigation path determined from the reference image 610 can be superimposed over the live image 620. In an example, based on the location of vessels in the duodenal papilla estimated from the reference image 610, position and rotation direction of a papillotomy knife can be determined, and superimposed over the live image 620 to guide papillotomy while avoiding cutting the vessels.

In the illustrated example, a navigation parameter status chart 630 can be displayed to show how well the real-time cannulation or navigation parameters (as determined from the live image 620) are in agreement with the reference parameter values. In case a real-time cannulation or navigation parameter substantially deviates from the reference value by an amount exceeding a specified margin, an alert or feedback may be generated. In the illustrated example, different colors are used to visually represent levels of agreement between the real-time cannulation or navigation parameters and the corresponding reference values. For example, a green color is to indicate the real-time parameter value being within the margin of reference value, yellow to indicate the borderline parameter value, and red to indicate the real-time parameter value exceeding the margin of the reference value and accordingly an elevated risk of tissue damage. Other forms of visual, audio, or haptic feedback or alert may be used to remind the operating physician to adjust the cannulation or navigation accordingly. In some examples, the output unit 542 may provide real-time recommendations for adjusting the cannulation or navigation. For example, if the cannula angle in the live image substantially deviates from the reference cannula angle, a message may pop up on the display, e.g., "Rotate the cannula 30 degree more in clockwise." Once the cannulation is completed successfully, an audio, visual, or haptic confirmation can be generated and provided to the physician.

Figure 7:
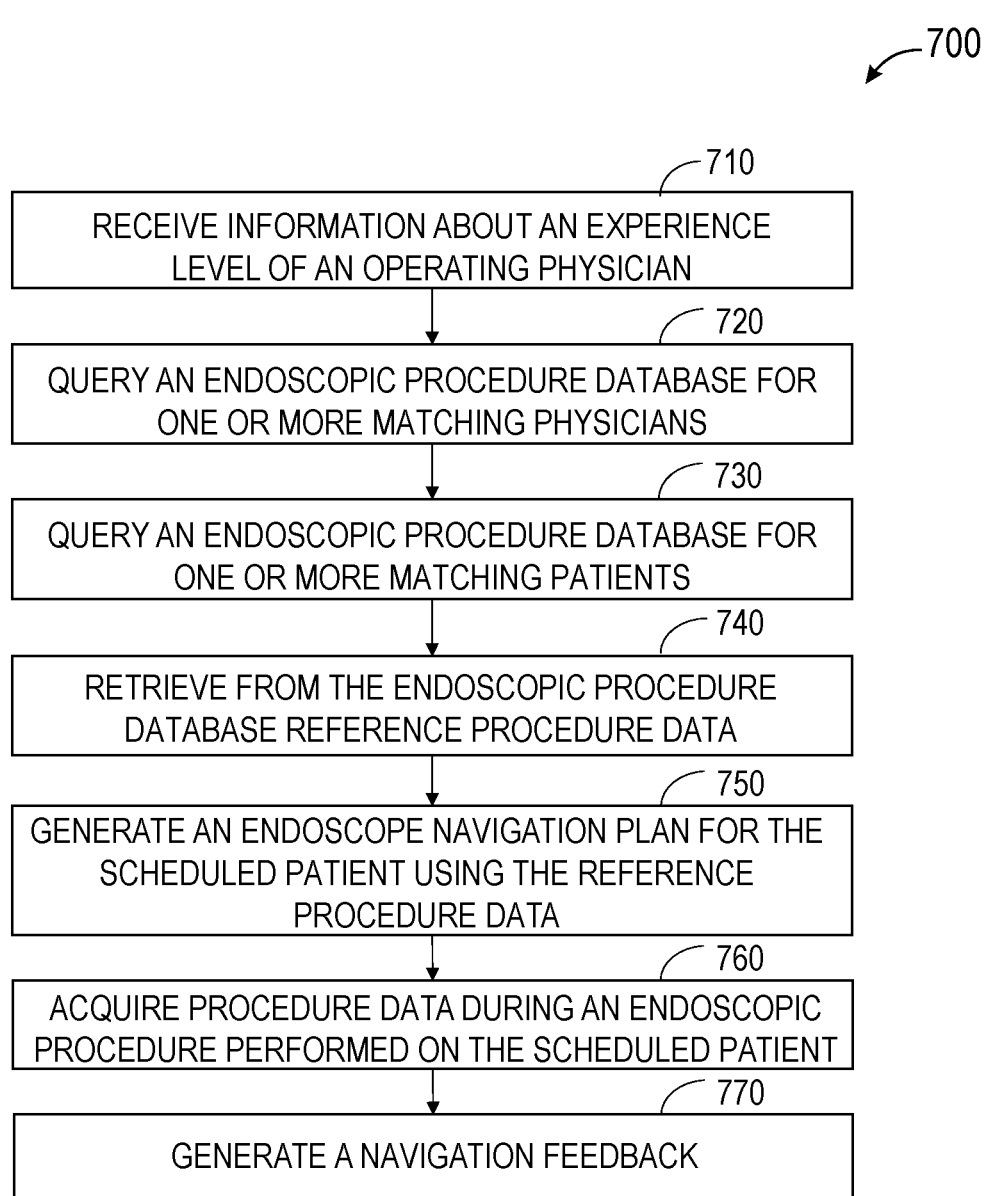
FIG. 7 is a flow chart illustrating an example method for planning an endoscopic procedure using past procedure data selected based at least on information about the operating physician.

FIG. 7 is a flow chart illustrating an example method 700 for planning an endoscopic procedure using past procedure data selected based at least on information about the operating physician. The method 700 may be implemented in and executed by the image-guided navigation system 500. Although the processes of the method 700 are drawn in one flow chart, they are not required to be performed in a particular order. In various examples, some of the processes can be performed in a different order than that illustrated herein.

At 710, information of an experience level of an operating physician performing the endoscopic procedure on a scheduled patient can be provided by a system user prior to the scheduled endoscopic procedure, or be retrieved automatically from an electronic medical record system. The operating physician's experience level can be represented by, for example, years in practice, the number of endoscopic procedures of the same type performed in the past (as the endoscope procedure to be performed on the scheduled patient, such as ERCP), and the success rate, among other information.

At 720, an endoscopic procedure database may be queried, such by using the search engine 510, to identify procedures performed by one or more physicians substantially matching the experience level of the operating physician. In an example, such matching physicians include those physicians having substantially similar experience levels to the operating physician for performing the type of endoscopic procedure to be performed on the scheduled patient. The endoscopic procedure database stores procedure data of past endoscopic procedures performed by a plurality of physicians on a plurality of patients. The stored procedure data can include, for each procedure, endoscopic images or videos showing patient anatomy, cannulation and endoscope navigation routes, progress of cannulation and navigation, or cannulation or navigation parameters obtained during the procedure or by offline analysis the endoscopic images or videos. The endoscopic procedure database 506 may also include physician information and optionally patient medical information for each of the stored past endoscopic procedures. The stored physician information can include the corresponding physician's experience level for performing endoscopic procedures of the same type. The stored patient medical information can include, for example, patient demographics, health conditions information and medical history, patient anatomy, image or image features, etc.

At 730, the endoscopic procedure database may optionally be queried to identify procedures performed on one or more patients substantially matching medical information of the scheduled patient, also referred to as matching patients. Examples of the medical information of the scheduled patient can include patient demographics, health condition and medical history, pre-existing disease, symptoms, location of lesion, anatomy information such as images (or video frames) obtained from imaging studies (e.g., X-ray, CT scans, MRI scans, ultrasound, nuclear medicine scans) prior to the scheduled endoscopic procedures, and endoscopic images of the anatomy of interest and endoscopic findings from previous endoscopic procedures.

At 740, procedure data corresponding to at least one endoscopic procedure performed by one of the matching physicians can be retrieved from the endoscopic procedure database. Such retrieved procedure data are also referred to as reference procedure data. In some examples, the reference procedure data correspond to at least one endoscopic procedure performed on at least one of the matching patients by at least one of the matching physicians.

At 750, an endoscope navigation plan can be generated for the scheduled patient using the reference procedure data. In an example, the reference procedure data may include reference endoscopic images or videos. Generating the navigation plan can include recognizing an anatomical target from the reference endoscopic images using an image processing algorithm, estimating values for one or more reference cannulation or navigation parameters, and determining a reference navigation path toward the anatomical target of interest. The reference cannulation or navigation parameters may be predetermined and stored in the endoscopic database. Alternatively, the reference cannulation or navigation parameters and the reference navigation path may be determined from the reference images or videos. Examples of the cannulation or navigation parameters can include a position of the endoscope distal portion relative to an anatomical target of interest, such as a distance from the endoscope distal portion to duodenal papilla, a heading direction of the endoscope distal portion relative to the anatomical target, an angle of a cannula or a surgical element used in cannulation, a protrusion amount of a cannula or a surgical element, a speed or force applied to the endoscope distal portion or a surgical element, a rotational direction or a cutting area of a surgical element, among others. In some examples, a machine-learning (ML) model may be trained to generate an endoscope navigation plan, including values for reference cannulation or navigation parameters and a reference navigation path. The ML model may be trained using supervised learning, unsupervised learning, or reinforcement leaning.

At 760, live procedure data can be acquired during the endoscopic procedure performed on the scheduled patient. The live procedure data be provided to the operating physician, such as displayed on an output unit. In an example, a reference image (an example of the reference procedure data obtained at step 740) can be concurrently displayed along with the live endoscopic image of the scheduled patient. For example, the reference image and the endoscopic image can be displayed side by side. Alternatively, the live endoscopic image can be transparently or semitransparently superimposed over the reference image.

In an example, visual indication of one or more of a visual indication of one or more of an anatomical target, a reference navigation path toward the anatomical target, or a progress of the endoscope toward the anatomical target along the reference navigation path may be displayed overlaid upon the live image, the reference image, or the superimposed image. The visual indication may take the format of include markers, annotations (icons, texts, or graphs), highlights, or animation, among other visual indicators.

At 770, an alert, a notification, or other types of human-perceptible feedback may be generated and provided to the operating physician to indicate the status or progress of the cannulation or navigation in reference to the navigation plan. The feedback can be in one or more forms of audio feedback, visual feedback, or haptic feedback. In an example, a distance to a critical anatomical target can be measured using a proximity sensor on the endoscope, or estimated from the endoscopic image. When the endoscope tip enters or comes closer to a "critical zone", the critical zone can be displayed in different colors to represent the proximity of the endoscope tip to the anatomical target, such as a green zone, a yellow zone, and a red zone as the endoscope gets closer and closer to the anatomical target. In an example, a haptic feedback includes vibration on a handle portion of the endoscope perceivable by the operating physician. The vibration can be automatically adjusted such that, for example, vibration becomes stronger as the distal portion of the endoscope gets closer to an anatomical critical zone.

Figure 8:
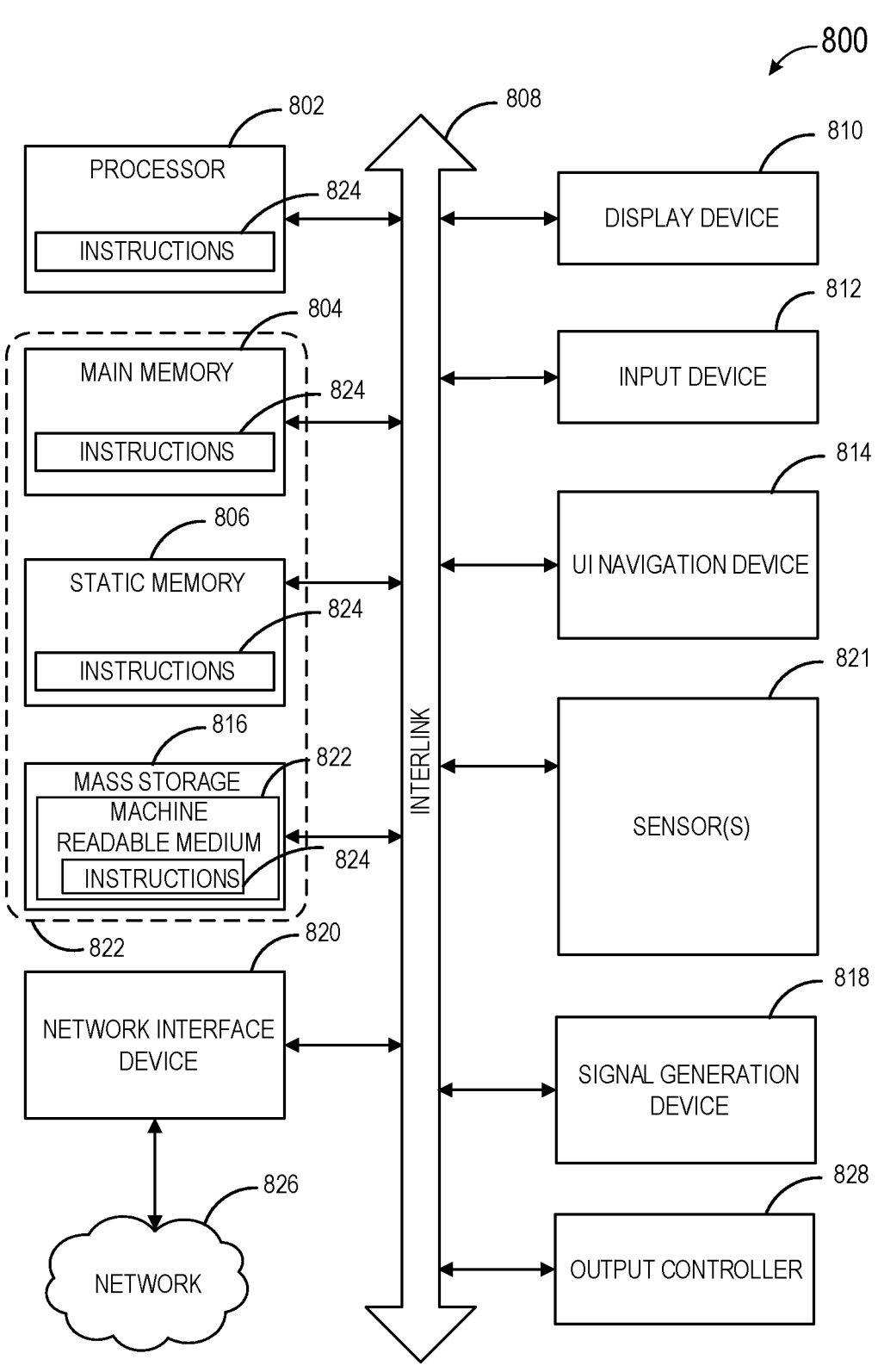
FIG. 8 is a block diagram illustrating an example machine upon which any one or more of the techniques (e.g., methodologies) discussed herein may perform.

FIG. 8 illustrates generally a block diagram of an example machine 800 upon which any one or more of the techniques (e.g., methodologies) discussed herein may perform. Portions of this description may apply to the computing framework of various portions of the image-guided navigation system 500, such as the image search engine 510, the navigation planning unit 520, and the navigation controller 550.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed)

network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensors. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine-readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 824 may further be transmitted or received over a communication network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communication network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for pre-operatively planning an endoscopic procedure of a type to be performed on a scheduled patient by an operating physician, the system comprising:

one or more processors; and memory, including instructions stored thereon that, when executed by the one or more processors, cause the one or more processors to:

determine or receive an experience level of the operating physician;

access an endoscopic procedure database to retrieve therefrom reference procedure data associated with one or more matching physicians having respective experience levels substantially matching the experience level of the operating physician, the endoscopic procedure database comprising procedure data of one or more past endoscopic procedures of the type performed by a plurality of physicians on a plurality of patients;

generate an endoscope navigation plan for the scheduled patient by applying the reference procedure data to a trained-learning model;

acquire, via a sensor, real-time procedure data including an endoscopic image taken during the endoscopic procedure performed on the scheduled patient;

correlate the acquired endoscopic image with a reference endoscopic image from the reference procedure data by identifying one or more anatomical landmarks to spatially align the acquired endoscopic image with the reference endoscopic image;

generate one or more real-time navigation parameters by applying the acquired endoscopic image and the correlation to the trained-learning model;

analyze one or more differences between the one or more real-time navigation parameters and at least one of the one or more reference endoscopic navigation parameters from the endoscopic navigation plan;

automatically adjust, via a navigation controller including feedback control circuitry configured to provide real-time feedback, the one or more real-time navigation parameters when the one or more real-time navigation parameters deviate from the one or more reference endoscopic navigation parameters by a specified amount, wherein the navigation controller further comprises one or more actuators configured to provide iterative real-time adjustment, based on data from the feedback control circuitry, of one or more physical positioning mechanisms of one or more components of an endoscope until the one or more real-time navigation parameters are within the specified amount; and display, via an output unit, a navigation parameter status chart showing different visual indicators to visually represent levels of agreement between the one or more real-time navigation parameters and the one or more reference endoscopic navigation parameters.

2. The system of claim 1, further comprising:

a sensor configured to acquire procedure data during the endoscopic procedure performed on the scheduled patient, wherein the output unit is configured to generate a navigation feedback using the acquired real-time procedure data and the endoscope navigation plan.

3. The system of claim 1, wherein the instructions further cause the one or more processors to:

access the endoscopic procedure database to retrieve therefrom procedure data associated with one or more procedures performed on one or more matching patients having medical information substantially matching medical information of the scheduled patient; and retrieve the reference procedure data corresponding to at least one endoscopic procedure performed on at least one of the one or more matching patients by at least one of the one or more matching physicians.

4. The system of claim 3, wherein the medical information of the scheduled patient includes at least one of demographic information or a health condition of the scheduled patient, and wherein the procedure data stored in the endoscopic procedure database include at least one of demographic information or a health condition of the plurality of patients, and wherein the instructions further cause the one or more processors to:

identify the one or more matching patients having respective demographic information or a respective health condition substantially similar to the demographic information or the health condition of the scheduled patient.

5. The system of claim 3, wherein the medical information of the scheduled patient includes anatomy information, wherein the procedure data stored in the endoscopic procedure database include anatomy information of the plurality of patients, and wherein the instructions further cause the one or more processors to:

identify the one or more matching patients having respective anatomy information substantially similar to the anatomy information of the scheduled patient.

6. The system of claim 5, wherein the medical information of the scheduled patient includes an image or one or more image features of an anatomical target, wherein the procedure data stored in the endoscopic procedure database include one or more respective images or one or more respective image features of the anatomical target obtained from the plurality of patients, and wherein the instructions further cause the one or more processors to:

identify the one or more matching patients having one or more respective images or one or more image features substantially similar to the image or one or more image features of the scheduled patient.

7. The system of claim 1, wherein to generate the endoscope navigation plan includes to estimate, from the reference procedure data, one or more reference endoscopic navigation parameters including at least one of:

a distance of an endoscope distal portion relative to an anatomical target;

a heading direction of the endoscope distal portion relative to the anatomical target;

an angle of cannula or a surgical element;

a protrusion amount of a cannula or a surgical element;

a speed or force applied to the endoscope distal portion or to a surgical element;

a rotational direction or a cutting area of a surgical element; or a projected navigation path toward the anatomical target.

8. The system of claim 7, wherein the reference procedure data include at least one reference endoscopic image taken during an endoscopic procedure performed by one of the one or more matching physicians, and wherein the instructions further cause the one or more processors to:

determine the one or more reference endoscopic navigation parameters using the at least one reference endoscopic image.

9. The system of claim 3, wherein the reference procedure data include at least one reference endoscopic image acquired during an endoscopic procedure performed on one of the one or more matching patients by one of the one or more matching physicians, and wherein the system further comprises:

a sensing apparatus configured to acquire procedure data including an endoscopic image acquired from the scheduled patient during the endoscopic procedure, wherein the output unit is configured to display the endoscopic image of the scheduled patient and the reference endoscopic image.

10. The system of claim 9, wherein the output unit is further configured to display one or more visual indications overlaid upon the endoscopic image of the scheduled patient, the one or more visual indications including at least one of:

an anatomical target;

a reference navigation path toward the anatomical target; or a progress of an endoscope toward the anatomical target along the reference navigation path.

11. The system of claim 9, wherein the output unit is configured to display the endoscopic image of the scheduled patient transparently or semi-transparently superimposed over the reference endoscopic image.

12. A method of planning an endoscopic procedure using an image-guided endoscopic system, the method comprising:

receiving information about an experience level of an operating physician performing an endoscopic procedure on a scheduled patient;

accessing an endoscopic procedure database to retrieve therefrom reference procedure data associated with one or more matching physicians having a respective experience level substantially matching the experience level of the operating physician, the endoscopic procedure database comprising procedure data of past endoscopic procedures performed by a plurality of physicians on a plurality of patients;

generating an endoscope navigation plan for the scheduled patient by applying the reference procedure data to a trained-learning model;

acquiring, via a sensor, real-time procedure data including an endoscopic image taken during the endoscopic procedure performed on the scheduled patient;

correlating the acquired endoscopic image with a reference endoscopic image from the reference procedure data by identifying one or more anatomical landmarks to spatially align the acquired endoscopic image with the reference endoscopic image;

generating one or more real-time navigation parameters by applying the acquired endoscopic image and the correlation to the trained-learning model;

analyzing one or more differences between the one or more real-time navigation parameters and at least one of the one or more reference endoscopic navigation parameters from the endoscopic navigation plan;

automatically adjusting, via a navigation controller including feedback control circuitry configured to provide real-time feedback, the one or more real-time navigation parameters when the one or more real-time navigation parameters deviate from the one or more reference endoscopic navigation parameters by a specified amount, wherein the navigation controller includes one or more actuators configured to provide iterative real-time adjustment, based on data from the feedback control circuitry, of one or more physical positioning mechanisms of one or more components of an endoscope until the one or more real-time navigation parameters are within the specified amount; and displaying, via an output unit, a navigation parameter status chart showing different visual indicators to visually represent levels of agreement between the one or more real-time navigation parameters and the one or more reference endoscopic navigation parameters.

13. The method of claim 12, further comprising:

acquiring procedure data during the endoscopic procedure performed on the scheduled patient; and generating a navigation feedback based on the acquired procedure data and the endoscope navigation plan.

14. The method of claim 12, further comprising:

accessing the endoscopic procedure database to retrieve therefrom procedure data associated with one or more procedures performed on one or more matching patients having medical information substantially matching medical information of the scheduled patient, wherein retrieving the reference procedure data includes retrieving procedure data corresponding to at least one endoscopic procedure performed on at least one of the one or more matching patients by at least one of the one or more matching physicians.

15. The method of claim 14, wherein the medical information of the scheduled patient includes one or more of:

demographic information;

a health condition;

anatomy information; or an image or one or more image features of an anatomical target.

16. The system of claim 1, wherein the trained-learning model is trained to establish a relationship between an endoscopic image and one or more endoscopic navigation parameters, and wherein the instructions further cause the one or more processors to:

compare the one or more real-time navigation parameters with at least one of the one or more reference endoscopic navigation parameters from the endoscopic navigation plan.

17. The system of claim 16, wherein the instructions further cause the one or more processors to:

train the trained-learning model using a training dataset comprising reference procedure data stored in the endoscopic procedure database, the reference procedure data including (i) multiple stored reference endoscopic images of one or more matching patients acquired during respective endoscopic procedures performed by the one or more matching physicians, and (ii) one or more stored endoscope navigation parameters for the respective endoscopic procedures, wherein the trained-learning model is trained to establish one or more variations between an anatomy of the scheduled patient in an endoscopic image and a corresponding endoscopic navigation parameter.

18. The system of claim 16, wherein the one or more processors is configured to:

generate the endoscope navigation plan including determining one or more reference endoscopic navigation parameters using the reference procedure data; and measure one or more real-time navigation parameters from the procedure data acquired from the scheduled patient, wherein the output unit is configured to:

generate a navigation feedback based on the comparison between the one or more real-time navigation parameters and the one or more reference endoscopic navigation parameters.

19. The system of claim 18, wherein the navigation feedback includes an alert to the operating physician in response to the one or more real-time navigation parameters deviate from the one or more reference endoscopic navigation parameters by a specific margin.

20. The system of claim 16, wherein the navigation controller is configured to automatically adjust the one or more real-time navigation parameters based on the comparison between the one or more real-time navigation parameters and the one or more reference endoscopic navigation parameters.

* * * * *